United States Patent [19]

Hach

[11] Patent Number: 4,645,746
[45] Date of Patent: Feb. 24, 1987

[54] DIGESTION PROCESS

[75] Inventor: Clifford C. Hach, Loveland, Colo.

[73] Assignee: Hach Company, Loveland, Colo.

[21] Appl. No.: 816,371

[22] Filed: Jan. 6, 1986

[51] Int. Cl.$^4$ .......................... G01N 1/28; G01N 33/00
[52] U.S. Cl. ...................................... 436/115; 436/79; 436/80; 436/81; 436/84; 436/103; 436/114; 436/175
[58] Field of Search ............... 436/111, 113, 114, 115, 436/149, 150, 151, 155, 157, 163, 164, 175, 179, 79, 80, 81, 84, 103

[56] References Cited

U.S. PATENT DOCUMENTS

| | | | |
|---|---|---|---|
| 2,644,743 | 7/1953 | Clevenger et al. | 422/104 |
| 3,450,501 | 6/1969 | Oberhardt | 436/69 X |
| 3,494,201 | 2/1970 | Roach | 422/100 X |
| 4,080,168 | 3/1978 | Abu-Samra et al. | 436/175 |
| 4,081,345 | 3/1978 | Tolg et al. | 436/149 X |
| 4,229,180 | 10/1980 | Christoffersen et al. | 436/114 |
| 4,347,216 | 8/1982 | Kawasaki et al. | 422/80 X |

FOREIGN PATENT DOCUMENTS

| | | | |
|---|---|---|---|
| 0011200 | 4/1973 | Japan | 436/113 |
| 0049085 | 4/1977 | Japan | 436/175 |
| 0143341 | 5/1920 | United Kingdom | 436/113 |
| 0292099 | 1/1971 | U.S.S.R. | 436/114 |

OTHER PUBLICATIONS

Krishnamurty et al., Atomic Absorption Newsletter, vol. 15, No. 3, pp. 68-70, 1976.
Razumov et al., Chemical Abstracts, vol. 96, Abstract No. 96:19370w, 1981.
Lowther, Chemical Abstracts, vol. 92, Abstract No. 92:211204g, 1980.
Kuznetsova et al., Industrial Laboratory (U.S.A.), vol. 42, No. 2, p. 207, 1976.
Ogg, Journal of the A.O.A.C., vol. 43, No. 3, pp. 689-693, 1960.
Bradstreet, "The Kjeldahl Method for Organic Nitrogen", Academic Press New York, 1965.
Miller et al., Anal. Chem., vol. 20, No. 5, pp. 481-488, 1948.
Lake et al., Anal. Chem., vol. 23, No. 11, pp. 1634-1638, 1951.
McKenzie et al., Australian J. Chem., vol. 7, pp. 55-70, 1954.
Shirley et al., Ind. Eng. Chem., vol. 17, No. 7, pp. 437-438, 1945.

Primary Examiner—Barry S. Richman
Assistant Examiner—Robert J. Hill, Jr.
Attorney, Agent, or Firm—Dean P. Edmundson

[57] ABSTRACT

An improved process for quantitatively determining nitrogen content or other elemental content in a wide variety of materials. The process avoids the use of conventional catalysts, is simpler and faster than previous techniques, and results in a very high degree of accuracy. The process involves the use of a hydrogen peroxide which is added to the digest continuously, while the digest is boiling, while refluxing with a fractionating column. The digestion process also enables quantitative determination of various elements other than nitrogen.

18 Claims, 3 Drawing Figures

DIGESTION PROCESS

FIELD OF THE INVENTION

This invention relates to digestion processes. More particularly, this invention relates to processes for quantitative determination of nitrogen and other elements in various substances.

BACKGROUND OF THE INVENTION

The need to quantitatively determine the amount of nitrogen and other elements contained in various organic compounds has been widespread for more than one hundred years. The need for determining the amount of nitrogen present led Johann Kjeldahl of Denmark to develop a method involving heating the substance in concentrated sulfuric acid and then adding powdered potassium permanganate. After addition of the permanganate the solution was diluted, transferred to a distilling flask, made alkaline, zinc added, and then distilled into standard acid. Potassium iodide and iodate were added to the distillate, and the liberated iodine was titrated with standard thiosulfate. See *The Kjeldahl Method for Organic Nitrogen*, R. B. Bradstreet (1965).

Others later learned that the speed of reaction in concentrated sulfuric acid was accelerated by the use of catalysts, such as the oxides of iron, mercury, manganese, bismuth, zinc, lead, and copper. Selenium was also touted as a good catalyst in the method, as was selenium dioxide-mercuric sulfate (1:1) and selenium dioxide-copper sulfate (3:1).

Because Kjeldahl's method required a considerable amount of time to digest the substance being tested, there was a desire to shorten the digestion time. This was eventually made possible when it was discovered that the addition of potassium sulfate raised the boiling point of the digestion mixture. Later it was found that the addition of various other sulfates and phosphates were also effective in raising the boiling point.

Hydrogen peroxide is reported to have been used in the Kjeldahl method as an oxidizing agent but with only limited success in aiding the digestion process. One researcher recommended the use of 30% hydrogen peroxide by mixing it with the organic matter to be treated, after which concentrated sulfuric acid is added slowly with shaking. Then potassium sulfate is added, and the mixture is then boiled. Modifications of the method by others involved adding various co-catalysts.

In another variation it was suggested to successively add 1-5 drops of 30% hydrogen peroxide to the carbonized digest, heat the digest until fumes appear, and reheat the digest after each addition. In yet another variation it was suggested to add peroxide after first heating the digest for five minutes over low flame. Then additional acid, copper sulfate catalyst and potassium sulfate are added and the resulting mixture heated until fumes are given off. Peroxide is then added until the solution remains blue and the digest is then heated for an hour with a high flame. Another suggested adding bromine after the organic matter has charred, reheating the digest, and again adding bromine with several drops of hydrogen peroxide; later peroxide is added alone.

It has also been suggested to heat the organic matter with oleum, then cool the digest after charring, followed by addition of peroxide to the cold digest. The digest is then heated for five minutes and the procedure repeated.

In yet another procedure concentrated sulfuric acid is added to the sample of organic matter and then allowed to stand for 15 minutes at room temperature before heating for several minutes. After cooling the digest, there are added 10-20 ml. of peroxide in small portions so as to avoid a large evolution of gas. After heating to expel the gas, the digest is boiled for five minutes and then the procedure is repeated until a clear solution results.

The various complexities and problems associated with the use of oxidizing agents in the Kjeldahl process have led researchers to conclude that it is better to depend upon the higher temperatures obtained by salt addition and an accelerated reaction rate through the use of catalysts than upon the use of an oxidizing agent to promote oxidation of organic matter. See p. 42 of *The Kjeldahl Method for Organic Nitrogen*, supra. The use of hydrogen peroxide has not been very satisfactory because of the time-consuming, tedious nature of its application and only partial success in improving the Kjeldahl method. None of the previously described methods using hydrogen peroxide have been proven to be faster or more accurate than other conventional Kjeldahl methods.

In the prior methods which utilized peroxide or peroxysulfuric acid, the concentration of the peroxide or peroxysulfuric acid was not maintained for sufficient time at a sufficiently high temperature to obtain any significant oxidation. The addition of hydrogen peroxide solution alone to hot sulfuric acid results in a violent decomposition at the surface of the acid layer with little benefit toward oxidation of the organic material dissolved in the sulfuric acid.

In U.S. Pat. No. 4,229,180 (Christoffersen) there is described a process for determining nitrogen in a sample, according to the Kjeldahl principle, in which an antimonate compound is used as a catalyst. Mention is made at Column 2 that the antimonate may be added as a powder, granulate, tablet, or as a solution in water or in a component which is to be added in the destruction anyway, such as hydrogen peroxide or sulfuric acid or mixtures thereof. Such patent does not describe pre-digesting the sample in sulfuric acid. Apparently the hydrogen peroxide is added, with concentrated sulfuric acid, to the sample along with the catalyst and salt (for increasing the boiling point) before the sample is heated. Then the destruction mixture is heated to 400° C., during which water and peroxide are evaporated or consumed.

Unfortunately, when the digest is heated at 410° C. or more there is a loss of nitrogen from the digest. As a result, the quantitative determination of nitrogen in the final digest will be erroneous. Also, when various salts are added to the digest in order to increase the boiling point of the sulfuric acid, such salts remain in the digest and prevent the digest from being used for quantitative determinations of elements (such as potassium) which are present in the added salts. Of course, the presence of catalyst has the same effect. Christofferson's method, using both catalysts and salts, requires temperatures and digestion times well outside that required in the process of the present invention (which does not use either catalysts or salts).

Yet another procedure is described in Analytical Chemistry, 20, pp. 481-488 (1948) in which the material sample is digested in sulfuric acid for five minutes, then cooled, after which two drops of hydrogen peroxide are added. Then the digest is heated again for two minutes and then cooled, after which another two drops of hydrogen peroxide are added. This process may be repeated several times. The process is tedious and time-consuming. The digestion time required for complete nitrogen recovery using such a process is several times longer than that obtainable by the process of the present invention.

Possibly the most advanced study of the use of peroxide is described in Australian J. Chem. 7, pp. 55–70 (1954) which reported only partial success, with difficulty, in using peroxide. The article reports that a fifty minute digestion (with sulfuric acid and peroxide) of the amino acid tryptophan resulted in only 98.3% recovery of nitrogen, and that digestion included ten separate additions of peroxide.

As stated in Analytical Chemistry, Vol. 23, No. 11, p. 1634 (1951), the temperature attained in digestion of the sample in the Kjeldahl procedure has been of prime importance. Too low a temperature either requires too long a digestion time or fails to give good results. Too high a temperature may result in loss of nitrogen from the digest. For samples containing nitrogen in pyridine ring structures, digestion at temperatures below 370° C. did not give quantitative recovery of pyridine with one hour digestion. At temperatures above 410° C. it was reported that nitrogen may be lost.

In Industrial and Engineering Chemistry, Vol. 17, pp. 437–438 (1945) it was reported that a digestion time of 2–4 hours was required for compounds such as pyridine, nicotine and nicotinic acid, using various types of catalysts.

In the Official Methods of Analysis of the Association of Official Analytical Chemists, the most commonly-used official method, it is recommended that any sample containing organic material be digested for at least two hours.

Such prior procedures are very undesirable for many situations, particularly where very accurate results are required or where time is of the essence in obtaining the results. Also, prior procedures are cumbersome or tedious. As a result, the person conducting the testing must follow the prescribed procedure carefully to avoid mistakes.

In my prior applications Ser. No. 06/583,984, filed Feb. 27, 1984, now abandoned, and Ser. No. 06/807,537, filed Dec. 12, 1985, I described a digestion process which avoids the use of catalysts and high temperatures. Such process involves the continuous addition to the digest of a reagent solution comprising a mixture of concentrated sulfuric acid and hydrogen peroxide. While such process represents a significant and important improvement over prior processes, the present invention provides even further significant improvements.

SUMMARY OF THE PRESENT INVENTION

In accordance with the present invention there is provided a simple and efficient process for the quantitative determination of nitrogen content and various other elemental content in various substances such as, for example, food products, animal feeds, grains, plant and animal tissue, fertilizers, protein, petroleum, coal, urea, amino acids, organic compounds including amines, amides, azo compounds, heterocyclic ring compounds such as pyridine and porphines.

The new process includes the steps of:
(a) placing a weighed sample of the material to be tested in a digestion flask;

(b) adding concentrated sulfuric acid to the flask to form a digest;

(c) heating the digest at a temperature and for a time sufficient to char the sample and bring the sulfuric acid to a boil at a temperature less than about 330° C.;

(d) continuously adding hydrogen peroxide to the digest while said digest is boiling;

(e) heating the digest at a temperature less than about 330° C., while refluxing with a fractionating column in a manner such that water vapor is removed and peroxide is returned to said digest, for a time sufficient to convert nitrogen present in the sample to ammonium ion, said time being less than about 10 minutes;

(f) optionally, cooling the digest;

(g) optionally, diluting the digest with water to form a test solution; and (h) quantitatively determining the nitrogen content, or other desired elemental content, from the test solution.

The process of the invention is simpler and faster than previous techniques. Surprisingly, this process is even faster and simpler than the process described in my prior filed applications. Yet the process results in a very high degree of accuracy for nitrogen analysis and is more accurate than many commercially utilized techniques. Also, since the present invention utilizes aqueous hydrogen peroxide solution, there is no need to prepare or use any reagent solution. Moreover, the process does not require the use of any catalysts. Since an aspirator is sufficient to remove fumes during digestion, there is no need to use a fume hood during the process. The process enables accurate nitrogen determinations on compounds often considered refractory when tested according to the traditional Kjeldahl method. Complete recovery of nitrogen in typical food and feeds can be accomplished after five minutes of digestion time, while difficult compounds such as lysine, pyridine and nicotinic acid require less than about 10 minutes of digestion time. This is significantly and unexpectedly faster than prior techniques (including my own prior process referred to above).

Still another significant advantage is that the resulting digest is also suitable for various chemical determinations other than nitrogen.

Because the temperature of the digest is maintained at a very low level (i.e., in the range of about 240° C. to 330° C.) and because of the use of a fractionating column, there is no loss of nitrogen or other desired element during the digestion process. Yet, surprisingly, all of the nitrogen in the sample is converted to ammonium ion so that its presence can be quantitatively determined easily and with a very high degree of accuracy.

BRIEF DESCRIPTION OF THE DRAWINGS

The invention is described in more detail hereinafter with reference to the accompanying drawings in which.

DETAILED DESCRIPTION OF THE INVENTION

Figure 1:
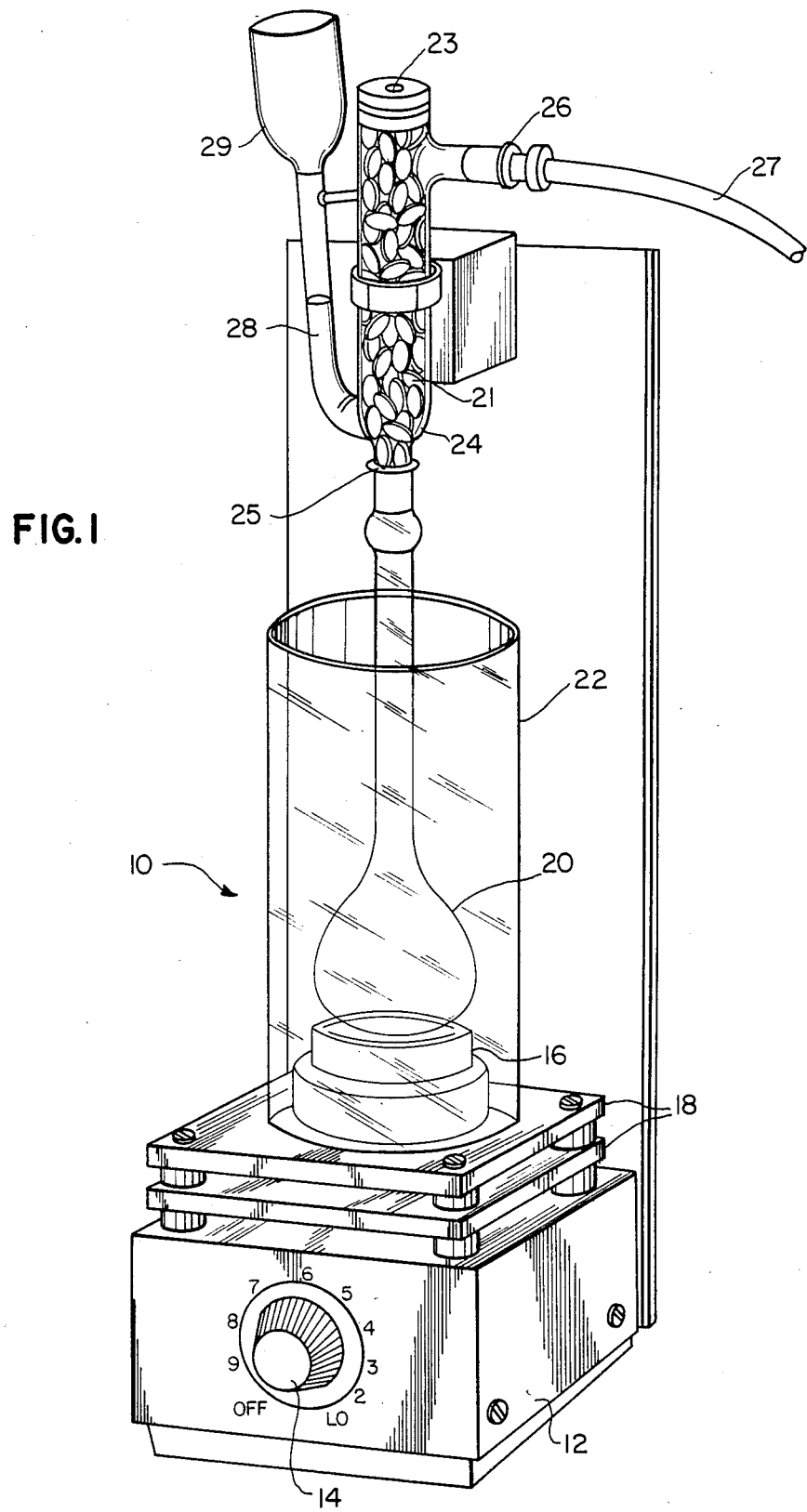
FIG. 1 shows one embodiment of apparatus which is useful in the practice of the present invention.

Thus, in FIG. 1 there is shown one embodiment of digestion apparatus 10 which is useful in the practice of this invention. The apparatus includes conventional electrical resistance heater assembly 12 which may be controlled as to temperature by means of control switch 14. The heated platen 16 is separated from the heater housing by means of asbestos layers 18.

Volumetric flask 20 is adapted to rest on the top of heated platen 16, as shown. Preferably a heat resistant glass chimney 22 surrounds the flask as a safety measure (i.e, to prevent the flask from being inadvertently bumped off the heated platen). A convenient size for the volumetric flask in the techniques of the present invention is 100 milliliters.

Mounted at the top of the volumetric flask is a packed fractionating column 24 which includes lower end 25 which is adapted to fit into the open top end of the flask. Side fitting 26 communicates with the upper end of column 24 and is adapted to be attached to a conventional aspirator tube 27.

Secured to column 24 is delivery tube 28 which communicates with the lower end of column 24. Fluid (i.e., hydrogen peroxide) may be introduced into tube 28 through capillary funnel 29 which sits on top of tube 28, as shown in FIG. 1. The fluid exits funnel 29 at a slow, controlled, uniform rate through the lower end thereof and into tube 28. Preferably the lower end of tube 28 is disposed such that the exit fluid flows along the interior surface of the column 24 and thence along the interior surface of the volumetric flask. Consequently, fluid which is fed to the digestion flask will interface and mix with the digest at an interior surface of the flask.

Fumes generated during the digestion process are drawn off through the packed column and out side fitting 26 to the aspirator. This avoids the need for an exhaust hood to contain the apparatus during the process.

Filling column 24 is a packing material 21. One embodiment of useful packing material is a plurality of individual glass helices. Of course, various other types of packing materials may be used instead, so long as there is a large amount of surface area, low thermal mass (so that it warms up rapidly during use), and reasonably uniform porosity such that the space between adjacent particles or material is large enough for water to pass through without clogging.

The packing material may be, for example, fibers (e.g., 0.01 to 0.05 inch in diameter; 0.25 to 0.75 inch in length), particles of all shapes (e.g., spheres 0.1 to 0.3 inch in diameter), beads (e.g., glass or ceramic), Teflon shavings, glass fibers, etc.

The purpose of the packing material is to provide a large surface area for vapor to condense on during the digestion process. The fractionating column is preferably about 100° C. at the top so that water vapor is allowed to escape, while hydrogen peroxide (having a higher boiling point) is condensed within the column and then flows downward and into the digestion flask again. Thus, the fractionating column effectively removes water vapor and returns hydrogen peroxide and sulfuric acid and other peroxy species (e.g., monoperoxysulfuric acid) to the digestion flask. This dramatically increases the residual peroxy concentration in the digest and even further speeds up the digestion process over prior methods. The fractionating column also traps any nitrogen species which might otherwise be carried out of the digestion flask.

The fractionating column typically and preferably contains packing material so that a large surface area is presented for condensing the peroxy species during digestion. However, if desired, other designs may be used for the fractionating column so long as sufficient surface area is presented to cause condensation of the peroxy species and nitrogen species during digestion while at the same time allowing water vapor to escape out the top portion of the column.

Aperture 23 in the top of column 24 enables air to pass therethrough into the top of the column, after which the air is drawn out through side fitting 26 to the aspirator as part of the fume removal system.

The process of the invention for quantitatively determining the nitrogen or other elemental content in a material sample begins with obtaining a weighed amount of the material to be tested. A very useful amount of a solid sample when using a 100 ml. digestion flask is 0.25 grams. If the material to be tested is a solid, the sample should be dry and preferably is finely divided. When the sample to be tested is a liquid, it is preferred to use about 1-5 grams of sample because it is easier to measure and handle.

The weighed sample is placed into the volumetric flask, after which concentrated sulfuric acid is added. Generally the amount of sulfuric acid added is approximately one to two milliliters when the sample weight is 0.25 grams and the sample is a carbohydrate. More acid is normally used when the sample contains considerable carbon-hydrogen compounds such as are found in petroleum products, coal, and the like. The important consideration is to use a sufficient amount of acid to wet the sample so that the sample will not bake to dryness during the process. No catalysts or other agents need be added.

The flask is then placed on the platen and heated at a temperature and for a time sufficient to char the sample and bring the sulfuric acid to a boil (about 300° to 330° C.). This normally only takes about two to five minutes, depending upon the sample size, the temperature to which it is heated, the type of material in the sample, etc. Then hydrogen peroxide (e.g., 50% aqueous solution) is continuously added to the boiling digestion mixture in the flask through the delivery tube 28. That is, the hydrogen peroxide is added as a sustained constant flow at a particular rate, while the digest is boiling. It is important to add the hydrogen peroxide in such a manner that the digest remains at or near the boiling temperature and that explosive decomposition or vaporization of the peroxide hydrogen peroxide is avoided. If the hydrogen peroxide was simply added dropwise onto the top surface of the digest there would be explosive decomposition; it has been noted that the advantages of the present technique are not obtained when the hydrogen peroxide is dropped directly onto the surface of the digest mixture. Rather, the advantages are only obtained when the hydrogen peroxide is added as a slow continuous stream such that large droplets are not presented where the hydrogen peroxide meets the digest.

The simplest manner for presenting the hydrogen peroxide to the digest in a controlled manner is to have the hydrogen peroxide flow slowly down the interior surface of the flask. In this approach the amount of hydrogen peroxide presented per unit of time is very limited and rapid vaporization or decomposition is avoided. Because only a small amount of hydrogen peroxide is presented per unit of time, the digest remains at or near its boiling point and this is very desirable. The hydrogen peroxide also boils as it mixes with the digest and this is effective in causing the desired oxidation of the material sample.

By adding the hydrogen peroxide solution in such a continuous and controlled fashion the high temperature of the boiling digestion mixture is maintained, yet a high enough concentration of peroxide is built up in the digest and maintained for the duration of the oxidation. The effectiveness of the digestion process is thus due to a combination of high temperature (i.e., up to about 330° C.), high concentration of peroxide, and long residence time of the peroxide in the digest.

This technique results in very rapid and effective digestion of the material sample without loss of nitrogen or other element being recovered. This technique is much more rapid and effective than prior techniques in which hydrogen peroxide was added in a series of increments or slugs. The present technique is also more rapid and simpler than my prior technique in which hydrogen peroxide is pre-mixed with sulfuric acid and then added to the digestion flask.

Figure 2:
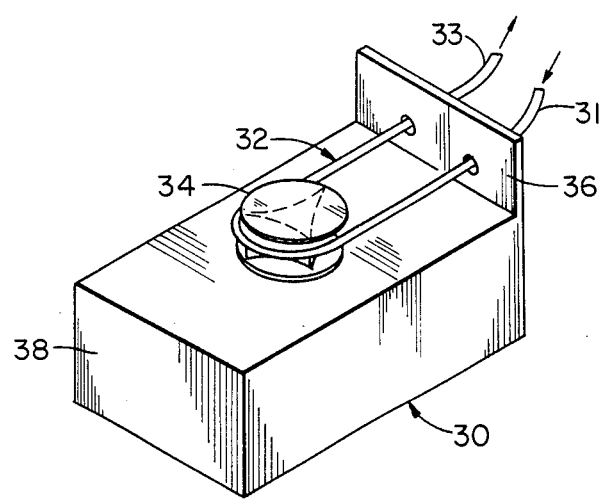
FIG. 2 is an isometric view of one embodiment of pumping apparatus which is useful in this invention.
Figure 3:
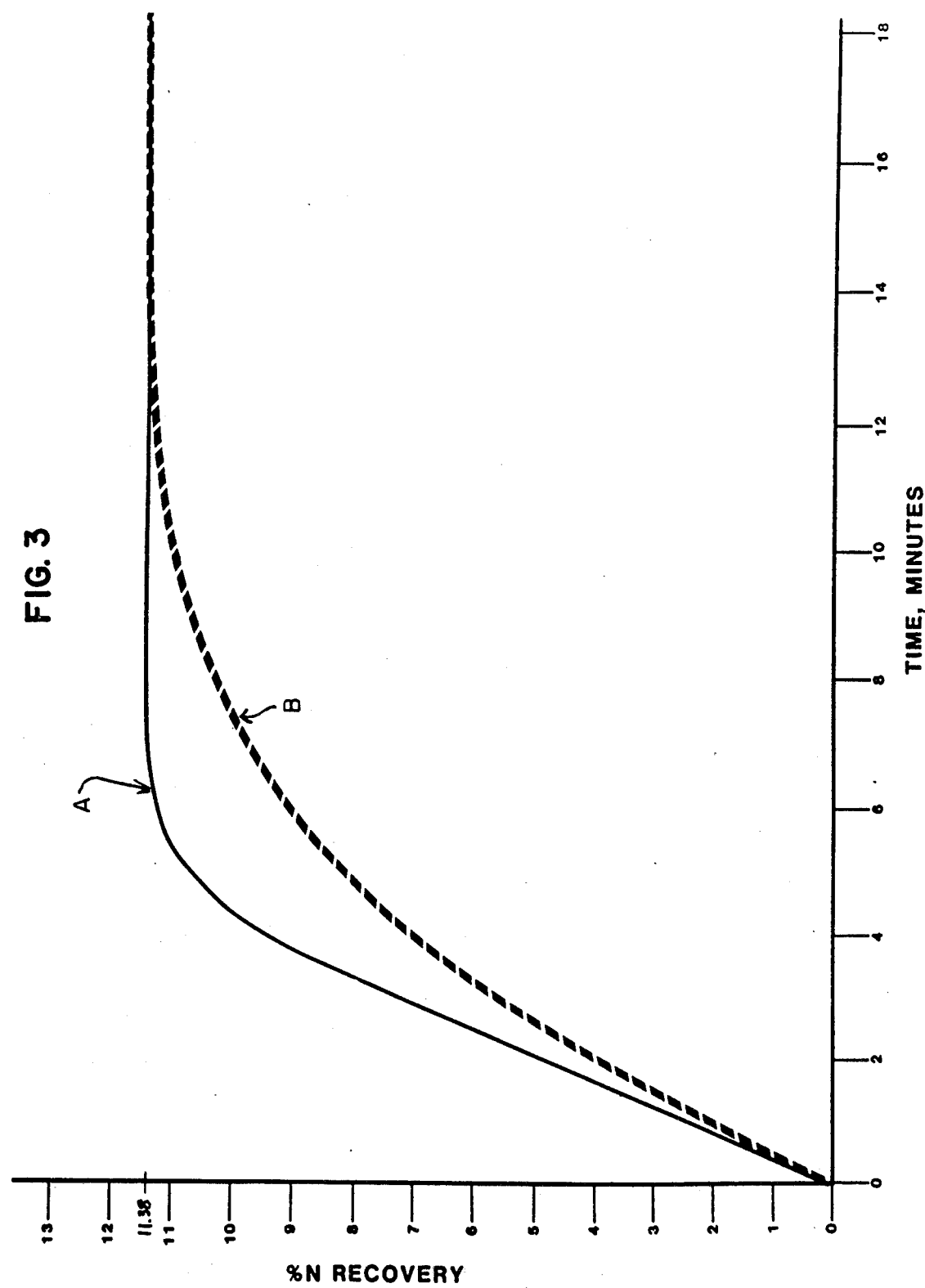
FIG. 3 is a graph illustrating the speed and accuracy of the process of this invention.

The hydrogen peroxide may be introduced into the top of funnel 29 by various means. For example, it may be simply poured into funnel 29 from a flask, graduated cylinder, etc. An alternative method is to pump the hydrogen peroxide directly into the top of delivery tube 28. Various types of pumping apparatus may be used for this purpose. The pumping speed may be adjusted, as desired, to obtain a controlled addition rate of hydrogen peroxide (e.g., in the range of approximately 0.5 to 10 milliliters per minute, preferably 1-3 milliliters per minute). In FIG. 2, for example, pumping apparatus 30 is shown which is useful for delivering the hydrogen peroxide to the funnel from a source container. The apparatus includes a length of flexible tubing 32 which is stretched tightly around a star wheel 34. The tube is secured in upright retention member 36, as shown. One end 31 of tube 32 is in communication with a source of the hydrogen peroxide while the opposite end 33 of tube 32 is operably connected to the funnel. The star wheel is rotatably driven by a motor within housing 38 at a predetermined rate. As the pointed projections of the star wheel successively squeeze tubing 32 closed, hydrogen peroxide from the source container is moved through tube 32 and out end 33. The speed of rotation of star wheel 34 determines the rate at which the hydrogen peroxide is pumped through tube 32. The speed may be adjusted, as desired, to obtain a controlled addition rate of hydrogen peroxide (e.g., in the range of approximately 0.5 to 10 milliliters per minute, preferably 1-3 milliliters per minute).

In the apparatus shown in FIG. 1, the hydrogen peroxide is added to the funnel 29 within delivery tube 28. The hydrogen peroxide then exits through the lower end of funnel 29 in a continuous manner at a constant rate and flows into delivery tube 28 and thence into the flask 20 along an interior surface thereof. In a typical example, when adding twenty milliliters of hydrogen peroxide, it takes ten minutes for it to flow through the funnel into the flask. The hydrogen peroxide is added continuously while the digest is refluxed.

The required digestion time will vary, depending upon the ease with which the sample is digested. The digestion time is typically in the range of one minute or less up to about ten minutes for very difficult materials. This is illustrated below in connection with Tables 1 and 2. These tables show the required digestion time, and amount of hydrogen peroxide used, when testing a wide variety of samples. One may determine the minimum digestion time required for other materials not present in the tables by preparing a digestion curve. This is done by digesting several identical samples for varying periods of time and then quantitatively measuring the amount of nitrogen recovered from each sample. From plotting the results on a graph of digestion time versus percent nitrogen recovered, one will readily observe the minimum digestion time required to reach the point on the curve where the percent nitrogen recovered is at its highest level. Of course, one may simply digest the sample for about 6 minutes and be confident that essentially all of the recoverable nitrogen has been obtained.

The digestion process of the present invention is very rapid as compared to conventional techniques. This is illustrated with the following comparisons for digestion times (including a normal period of approximately 5 minutes to char the sample before addition of hydrogen peroxide):

| Compound | Digestion Time Required | |
|---|---|---|
| | Conventional | Present Invention |
| Nicotinic acid | 180–240 minutes | 11 minutes |
| Tryptophan | 55 | 8.2 |

The speed and accuracy of the process of this invention is further illustrated in the graph of FIG. 2. This graph shows the digestion times required for nicotinic acid when using the process of this invention (curve A) and the process of my prior invention (curve B) which is described in copending application Ser. No. 06/807,537. The conventional process, using selenium and mercury catalysts as well as potassium sulfate addition, as described in Analytical Chemistry, 17, pp. 437–438, requires approximately three hours of digestion of nicotinic acid in order to obtain a nitrogen determination approaching theoretical. Using the process of this invention it is only necessary to digest for approximately 6-7 minutes (after the charring of the sample) in order to obtain a nitrogen determination approaching theoretical. Using the process of my prior invention referred to above it is necessary to digest for approximately 14-15 minutes. Thus, the process of the present invention is considerably faster.

After the digestion process has been completed the digest and the flask are preferably cooled (e.g., by placing the flask in warm water and then cooler water so that the flask does not break, or the flask may be air cooled). After the digest has been adequately cooled, the digest may be diluted with water to form a test solution, if desired. Because the flask is volumetric, all that is required is to fill the flask to the fill line with desired diluent such as water or other solvent.

However, it is not necessary to cool the digest or dilute it as described above in order to measure the nitrogen content. For example, a small aliquot of the digest may be removed from the digestion flask and analyzed in accordance with conventional techniques for nitrogen content. Optionally, the digest may be diluted with a solvent to form a test solution. Still other alternatives for analyzing the digest directly, without adding diluents, include distillation or use of an autotitrator.

Of course, it is also possible to analyze the digest for various elements other than nitrogen. Because no salts or catalysts were added to the digestion flask during the process of this invention, the resulting digest is suitable for quantitative analysis of various materials present therein. For example, the digest may be diluted with desired diluent and examined for elements such as nitrogen, phosphorus, potassium, manganese, calcium, magnesium, zinc, iron, copper, cobalt, or other elements.

After a test solution has been prepared as described above, it may be used in accordance with known techniques for quantitatively determining the amount of nitrogen present. A preferred technique for determining nitrogen content involves a colorimetric method known as nesslerization. Organic nitrogen present in the digest sample has been converted to ammonium nitrogen. The Nessler reagent, a strongly alkaline solution of sodium or potassium mercuric iodide, is added to an aliquot of the digest sample and it reacts with the ammonium nitrogen to form a yellow color. The intensity of the yellow color is directly proportional to the amount of ammonium nitrogen present. Of course, other types of colorimetric procedures may be used instead.

Another method for determining the nitrogen content in the digest is known as a titrimetric method. The ammonia in the digest is distilled out and trapped in a solution which is then titrated with acid to determine the amount of ammonia present.

In yet another known technique the ammonia in the digest is determined potentiometrically. An ammonia ion selective electrode is used in operable connection with a pH/mV meter. Other conventional potentiometric methods may also be used.

In the table below various specific materials are listed along with the digestion times required for each (for 99% recovery of nitrogen) when using (1) the process (A) of my prior invention as described in application Ser. No. 06/807,537, and (2) the process (B) of this invention with a fractionating column:

| Sample | Digestion Times Required (minutes) | |
| --- | --- | --- |
|  | Process A | Process B |
| Aspartic Acid | 1.0 | 0.6 |
| Whole-wheat Flour | 2.0 | 1.0 |
| Alanine | 2.0 | 1.2 |
| Soybean meal | 3.3 | 2.3 |
| Tryptophan | 4.7 | 3.9 |
| Bovine liver | 5.5 | 4.0 |
| Feather meal | 5.5 | 3.6 |
| Methionine | 6.3 | 4.2 |
| Instant Dry Milk | 6.8 | 2.9 |
| Cattle Feed | 9.6 | 4.9 |
| Fish meal | 10.0 | 5.9 |
| Nicotinic acid | 12.5 | 6.0 |
| Lysine | 15.0 | 4.7 |

The process of the invention is not only very rapid and simple, it is extremely accurate and produces more reliable results than observed using the conventional Kjeldahl method. Furthermore, the digestion process does not contaminate the sample because no salts or catalysts are added. Therefore, the digestion process produces a digest suitable for the determination of many other elements present in the sample besides nitrogen.

The digestion process of the invention is also very useful in providing a digest which is suitable for direct aspiration in conventional atomic absorption spectroscopy methods. For example, the digestion process can be used to form a suitable digest from organic and inorganic materials such as sewages, waters, sediments, sludges, industrial and domestic waste products, soils, coal, oils, wood, leather, hair, rubber, plastics, etc.

As a comparative example, nicotinic acid (0.25 gram) was digested in accordance with the present invention using the apparatus shown in FIG. 1. The sample was heated in 3 milliliters of concentrated sulfuric acid at about 320° C. for 5 minutes, after which heating continued at the same level while 12 milliliters of hydrogen peroxide (50% solution) was added over a period of about 4.5 minutes. The sample was heated for approximately one more minute at that temperature. Then the sample was cooled, diluted with water, and analyzed colorimetrically to reveal 11.38% nitrogen (100% recovery). Then a similar sample of nicotinic acid was digested using the apparatus disclosed in FIG. 1 of my prior application Ser. No. 06/807,537, following the same procedure. The hydrogen peroxide (50% solution) was added in the same amount (12 ml.) and at the same rate as in the first example.

The only difference between the two runs is that the apparatus used in the first example included a fractionating column (which allowed moisture vapor to escape while peroxy species were returned to the digest) while the apparatus used in the second example did not include a fractionating column. In the second example the analysis of the final digest revealed only 8.92% nitrogen (78.4% recovery).

Consequently, the process of my prior invention does not produce accurate results when hydrogen peroxide is simply substituted for the reagent solution of hydrogen peroxide/sulfuric acid. In the present invention, utilizing the fractionating column in the manner described herein, the use of hydrogen peroxide produces extremely accurate results in less time than has previously been possible.

What is claimed is:

1. A process for digesting a material sample, the process comprising the steps of:
   (a) placing a weighed amount of a material sample in a digestion flask;
   (b) adding concentrated sulfuric acid to said flask to form a digest;
   (c) heating said digest at a temperature and for a time sufficient to char said material sample and bring said digest to a boil at a temperature less than about 330° C.; and
   (d) continuing to boil said digest at said temperature less than about 330° C., while simultaneously continuously adding hydrogen peroxide to said digest and refluxing with a fractionating column in a manner such that water vapor is removed and hydrogen peroxide is returned to said digest, for a time sufficient to convert all nitrogen present in said material sample to ammonium ions, said time being less than about 10 minutes, and wherein said hydrogen peroxide enters said digest along an interior surface of said flask such that a slow continuous stream of said hydrogen peroxide is presented where said hydrogen peroxide meets said digest.

2. A process in accordance with claim 1, wherein said material sample is dry and finely divided.

3. A process in accordance with claim 1 wherein said digest is cooled and diluted with water after step (d) to form a test solution.

4. A process in accordance with claim 1, wherein said hydrogen peroxide is added to said digest by means of a pump.

5. A process in accordance with claim 1, wherein said fractionating column is a packed column.

6. A process in accordance with claim 5, wherein said packed column comprises a plurality of glass helices.

7. A process for the quantitititative determination of the nitrogen content in a material sample, the process comprising the steps of:
(a) placing a weighed amount of a material sample in a digestion flask;
(b) adding concentrated sulfuric acid to said flask to form a digest;
(c) heating said digest at a temperature and for a time sufficient to char said material sample and bring said digest to a boil at a temperature less than about 330° C.;
(d) continuing to boil said digest at said temperature less than about 330° C., while simultaneously continuously adding hydrogen peroxide to said digest and refluxing with a fractionating column in a manner such that water vapor is removed and hydrogen peroxide is returned to said digest, for a time sufficient to convert all nitrogen present in said material sample to ammonium ions, said time being less than about 10 minutes, and wherein said hydrogen peroxide enters said digest along an interior surface of said flask such that a slow continuous stream of said hydrogen peroxide is presented where said hydrogen peroxide meets said digest; and
(e) quantitatively determining the nitrogen content in said material sample by quantitatively detecting ammonium ions in said digest.

8. A process in accordance with claim 7, wherein said material sample is dry and finely divided.

9. A process in accordance with claim 7, wherein ammonium ions in said digest are quantitatively determined by means of titrimetric analysis.

10. A process in accordance with claim 7, wherein ammonium ions in said digest are quantitatively determined by means of potentiometric analysis.

11. A process in accordance with claim 7, wherein said digestion flask is a volumetric flask.

12. A process in accordance with claim 7, wherein said hydrogen peroxide is added to said digest by means of a pump.

13. A process in accordance with claim 7, wherein said fractionating column is a packed column.

14. A process in accordance with claim 13, wherein said packed column comprises a plurality of glass helices.

15. A process in accordance with claim 7, wherein the quantitative determination step includes cooling said digest and diluting said digest with water to form a test solution.

16. A process in accordance with claim 15, wherein quantitative determinations for elements are conducted using said test solution, wherein said elements are selected from the group consisting of phosphorus, potassium, manganese, calcium, magnesium, zinc, iron, copper and cobalt.

17. A process in accordance with claim 15, wherein the quantitative determination step also includes quantitatively determining ammonium ions in said test solution by means of colorimetric analysis.

18. A process in accordance with claim 17, wherein Nessler reagent is added to said test solution prior to colorimetric analysis.

* * * * *